(12) United States Patent
Taniguchi et al.

(10) Patent No.: US 8,802,008 B2
(45) Date of Patent: Aug. 12, 2014

(54) DISPENSING NOZZLE FOR AUTOMATIC ANALYZER, AND AUTOMATIC ANALYZER INCLUDING SAME

(75) Inventors: Shinichi Taniguchi, Tokyo (JP); Akihiro Nojima, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 78 days.

(21) Appl. No.: 13/515,017

(22) PCT Filed: Nov. 26, 2010

(86) PCT No.: PCT/JP2010/071079
§ 371 (c)(1),
(2), (4) Date: Jun. 11, 2012

(87) PCT Pub. No.: WO2011/070919
PCT Pub. Date: Jun. 16, 2011

(65) Prior Publication Data
US 2012/0251393 A1 Oct. 4, 2012

(30) Foreign Application Priority Data
Dec. 11, 2009 (JP) ................................ 2009-281539

(51) Int. Cl.
| | | |
|---|---|---|
| *G01N 21/00* | (2006.01) | |
| *B05D 3/02* | (2006.01) | |
| *B05D 3/12* | (2006.01) | |
| *G01N 35/02* | (2006.01) | |
| *C23C 2/00* | (2006.01) | |
| *G01N 35/10* | (2006.01) | |
| *G01N 31/00* | (2006.01) | |
| *B01L 3/02* | (2006.01) | |
| *G01N 35/04* | (2006.01) | |

(52) U.S. Cl.
CPC .............. *G01N 35/026* (2013.01); *G01N 35/04* (2013.01); *B01J 2219/00612* (2013.01); *C23C 2/00* (2013.01); *G01N 35/1002* (2013.01)
USPC ............. 422/65; 427/2.11; 427/241; 422/509

(58) Field of Classification Search
CPC ............................. G01N 35/026; G01N 3/045
USPC .................................................... 422/65, 509
See application file for complete search history.

(56) References Cited

U.S. PATENT DOCUMENTS 4,357,301 A * 11/1982 Cassaday et al. ................ 422/64
4,868,048 A * 9/1989 Barr et al. ...................... 428/328
(Continued)

FOREIGN PATENT DOCUMENTS

| CN | 1651921 A | 8/2005 |
|---|---|---|
| CN | 1720096 A | 1/2006 |

(Continued)

OTHER PUBLICATIONS

China Office Action of Appln. No. 201080055689.8 dated Aug. 30, 2013.

(Continued)

*Primary Examiner* — Jill Warden
*Assistant Examiner* — Brittany Fisher
(74) *Attorney, Agent, or Firm* — Antonelli, Terry, Stout & Krause, LLP.

(57) ABSTRACT

An automatic analyzer for analyzing samples, such as urine and blood, is adapted so that analysis measured values are not affected by carry over by a repeatedly used dispensing nozzle. Coating the surface of the dispensing nozzle with a chemisorbed polyethylene glycol derivative forms a molecular layer that inhibits the adsorption of biopolymers, to reduce carry over by the dispensing nozzle.

6 Claims, 9 Drawing Sheets

(56) References Cited

U.S. PATENT DOCUMENTS

| | | |
|---|---|---|
| 2003/0080087 A1* | 5/2003 | Stelzle .......................... 216/27 |
| 2003/0180466 A1* | 9/2003 | Rohrbaugh et al. ....... 427/372.2 |
| 2003/0225362 A1 | 12/2003 | Currie et al. |
| 2004/0110276 A1 | 6/2004 | Amontov et al. |
| 2005/0062801 A1* | 3/2005 | Kato et al. .................... 347/45 |
| 2005/0242117 A1 | 11/2005 | Yoshida et al. |
| 2007/0104615 A1* | 5/2007 | Hanafusa et al. .............. 422/65 |
| 2008/0050279 A1* | 2/2008 | Fujita ............................. 422/67 |
| 2008/0254995 A1* | 10/2008 | Kim et al. ......................... 506/4 |
| 2009/0258049 A1* | 10/2009 | Klein et al. ................... 424/423 |
| 2010/0150782 A1* | 6/2010 | Fukushima et al. ....... 422/82.05 |

FOREIGN PATENT DOCUMENTS

| | | |
|---|---|---|
| JP | 3-75827 | 12/1991 |
| JP | 9-304243 | 11/1997 |
| JP | 2002-162404 | 6/2002 |
| JP | 3330579 | 7/2002 |
| JP | 2004-522460 | 7/2004 |
| JP | 2006-509201 | 3/2006 |
| JP | 2007-85930 | 4/2007 |

OTHER PUBLICATIONS

Abraham Ulman, Formation and Structure of Self-Assembled Monolayers, Chemical Review, 1996, pp. 1533-1554, vol. 96, No. 4.

Kevin L. Prime et al., Adsorption of Proteins onto Surfaces Containing End-Attached Oligo(ethylene oxide): A Model System Using Self-Assembled Monolayers, Journal American Chemical Society, 1993, pp. 10714-10721, vol. 115, No. 23.

C. M. Pradier et al., Adsorption of Bovine Serum Albumin on chromium and Molybdenum Surfaces Investigated by Fourier-Transform Infrared Reflection-Absorption Spectroscopy (FT-IRRAS) and X-ray Photoelectron Spectroscopy, Journal of Physical Chemistry B, 2003, pp. 6766-6773, vol. 107, No. 28.

\* cited by examiner

DISPENSING NOZZLE FOR AUTOMATIC ANALYZER, AND AUTOMATIC ANALYZER INCLUDING SAME

TECHNICAL FIELD

The present invention relates to a dispensing nozzle for an automatic analyzer, and an automatic analyzer including the same.

BACKGROUND ART

In clinical examination for medical diagnosis, protein, sugar, lipid, enzyme, hormone, inorganic ions, disease markers, and the like in biological samples, such as blood and urine, are biochemically analyzed and immunologically analyzed. In clinical examination, it is necessary to treat a plurality of examination items with high reliability at high speed, and therefore, most of them are performed by an automatic analyzer. As the automatic analyzer, for example, a biochemistry analyzer that performs biochemical analysis by using, as an object to be analyzed, a reaction solution obtained by mixing a sample, such as serum, with the desired reagent for reaction, and measuring the absorbance of the reaction solution is known. A biochemistry analyzer of this type includes containers containing samples and reagents, and reaction Cells into which the samples and the reagents are to be injected, and includes dispensing mechanisms including dispensing nozzles for automatically injecting the sample and the reagent into the reaction Cell, an automatic stirring mechanism having a stirring bar for mixing the sample and the reagent in the reaction Cell, a mechanism for measuring the absorbance of the sample during reaction or after the completion of the reaction, an automatic washing mechanism for sucking and discharging the reaction solution after the completion of the measurement and washing the reaction Cell, and the like (for example, Patent Literature 1).

In such an automatic analyzer, generally, a large number of samples and reagents are dispensed in turn by the dispensing nozzles. For example, the sample dispensing nozzle takes a predetermined amount of a sample from a container containing the sample, such as a blood collection tube, and discharges the sample into a reaction Cell for the reaction of a reagent. The reagent dispensing nozzle discharges into the reaction Cell a predetermined amount of a reagent taken from a container containing the reagent. At this time, if the components of the dispensed liquid remaining on the dispensing nozzle surface are mixed into the next dispensed liquid, the measurement result may be affected. This is referred to as carry over.

The problem of carry over is deeply related to a demand for trace amounts of samples and reagents in the field of automatic analyzers in recent years. With the increase of the number of analysis items, the amount of a sample that can be used for one analysis item becomes smaller. The sample itself is precious and cannot be prepared in a large amount in some cases, and there is also a demand for higher sensitivity. In addition, as the analysis content becomes more sophisticated, generally, the reagent becomes more expensive, and there is a requirement for trace amounts of reagents also in terms of cost. Due to the increase of such a demand for trace amounts of samples and reagents, the diameter of the dispensing nozzle becomes smaller, and the outer diameter of the tube is about 0.5 mm. A very small nozzle diameter increases the proportion of the surface area to the volume of a dispensed solution. Therefore, the importance of controlling the adsorption of substances on the dispensing nozzle surface to reduce carry over increases.

In addition, when a sample for the analysis of biochemistry items, and immunity items with a wide measurement concentration range is taken from the same container and measured, it is required to reduce carry over between samples by a dispensing nozzle as much as possible.

In order to reduce carry over, conventionally, washing with pure water or a detergent containing a surfactant has been carried out (Patent Literature 2). A method of deactivating adhering sample residues with active oxygen is also known (Patent Literature 3). A method using a disposable nozzle (disposable tip), which can be thrown away after one use, is also known as one of methods for solving carry over.

XPS (X-ray photo electron spectroscopy) and the like are widely used for the quantification and composition analysis of chemical substances adsorbed on a surface, and, for example, analysis is performed for the composition of monomolecular films, such as self-assembled monolayers, and the quantification of chemical species (Non Patent Literatures 1 and 2). Like these, quantification can be performed by XPS also for the quantification of protein remaining on a surface (Non Patent Literature 3).

CITATION LIST

Patent Literature
Patent Literature 1: JP Patent No. 1706358
Patent Literature 2: JP Patent Publication (Kokai) No. 2007-85930 A
Patent Literature 3: JP Patent No. 3330579
Non Patent Literature
Non Patent Literature 1: Chemical Reviews, 96, pp. 1533-1554 (1996)
Non Patent Literature 2: Journal of the American Chemical Society, 115, pp. 10714-10721 (1993)
Non Patent Literature 3: The Journal of Physical Chemistry B, 107, pp. 6766-6773 (2003)

SUMMARY OF INVENTION

Technical Problem

In the washing with pure water or a detergent containing a surfactant, the washing of biopolymers typified by protein may be difficult. In the method of deactivating adhering sample residues with active oxygen, the deactivated sample residues are deposited on the surface, and therefore, the dispensing nozzle cannot withstand a long period of use. In addition, in the disposable nozzle, it is difficult to form a fine structure in terms of strength and processing precision. In addition, a problem of the use of disposable nozzles is that it produces a large amount of waste to increase the environmental load.

It is an object of the present invention to provide the sample dispensing nozzle of an automatic analyzer in which the cleanliness of the surface is increased to promote the reduction of carry over, without using a disposable nozzle, and an automatic analyzer using the same.

Solution to Problem

For analysis items for which the necessity to avoid carry over is high, the analysis components are often biopolymers, such as protein. Therefore, in order to reduce carry over, a solution is to inhibit biopolymers, such as protein, from remaining on the surface of the dispensing nozzle. In the present invention, for this purpose, a molecule that inhibits nonspecific adsorption of biomolecules, such as a sample, is immobilized on the nozzle surface. In addition, in the immobilization of the above molecule, chemisorption, particularly a covalent bond, on the surface is used. At this time, the material of the nozzle is not limited as long as the molecule that inhibits nonspecific adsorption is immobilized on the outermost surface of the nozzle.

Chemisorbing and coating a polyethylene glycol (PEG) derivative on the dispensing nozzle surface inhibits the adsorption of living body-derived polymers, such as protein, to solve the above problems. Here, chemisorption means a mode of adsorption on a solid surface with a heat of adsorption of about 20 to 100 kcal/mol, which is caused by a chemical bond, such as a covalent bond or an ionic bond. Chemisorption is distinguished from physisorption generally with a heat of adsorption of 10 kcal/mol or less, using Van der Waals force as bonding force. The polyethylene glycol derivative is hydrophilic and inhibits the adsorption of biopolymers, such as protein, by its steric repulsive force. The PEG derivative has the highest protein adsorption inhibition effect. This is because, generally, when a nonionic water-soluble polymer is coated on a material surface, the surface charge is suppressed while the hydrophilicity of the substance surface is improved. In addition to such properties, the fact that PEG has almost no toxicity is also important for clinical applications.

From the requirements that the required number of ethylene oxide ($-C_2H_4O-$) groups is 2 or more and that the molecular interaction for molecules to be arranged is sufficient, it is desired that the molecular weight of the PEG derivative is 100 or more. On the contrary, if the steric repulsive force between molecules is too large, the amount of adsorption of the PEG derivative on the surface is reduced. Therefore, it is desired that the molecular weight of the PEG derivative is 20000 or less. The chemical structure of the coating PEG derivative need not be single and may be a mixture.

The automatic analyzer of the present invention includes a plurality of sample containers each containing a sample; a plurality of reagent containers each containing a reagent; a plurality of reaction Cells into which the samples and the reagents are to be injected; a sample dispensing mechanism including a sample dispensing nozzle and dispensing the samples in the sample containers into the reaction Cells; and a reagent dispensing mechanism including a reagent dispensing nozzle and dispensing the reagents in the reagent containers into the reaction Cells, wherein the sample dispensing nozzle has a silicon oxide layer on a surface thereof, and a silicon derivative having polyethylene glycol, represented by the following general formula:

$Si-R_1-(OCH_2CH_2)_n-O-R_2$ (n is a positive integer of 2 or more, $R_1$ is a hydrocarbon group, and $R_2$ is H or $CH_3$)

is chemisorbed on the silicon oxide layer.

In addition, a method for manufacturing a dispensing nozzle for an automatic analyzer according to the present invention includes the steps of:
(a) forming a silicon oxide layer on a surface of a dispensing nozzle using sputtering or drug solution application and drying;
(b) washing the silicon oxide layer formed on the surface of the dispensing nozzle;
(c) immersing the washed dispensing nozzle in a solution of a polyethylene glycol derivative having a silanol group precursor, represented by the following general formula:

$R_1R_2R_3Si-R_4-(OCH_2CH_2)_n-O-R_5$ ($R_1$, $R_2$, and $R_3$ are substituents on silicon, $R_4$ is a hydrocarbon group, $R_5$ is H or $CH_3$, and n is a positive integer of 2 or more);
(d) washing the treated surface of the dispensing nozzle with a solvent; and
(e) drying the washed surface of the dispensing nozzle.

Advantageous Effects of Invention

According to the present invention, the adsorption of biopolymers, such as protein, on the dispensing nozzle can be inhibited. Therefore, carry over during dispensing operation can be reduced, and the analysis reliability of the automatic analyzer is improved, thereby contributing to trace amounts of samples and reagents and also contributing to the reduction of the running cost of the automatic analyzer.

DESCRIPTION OF EMBODIMENTS

Figure 1:
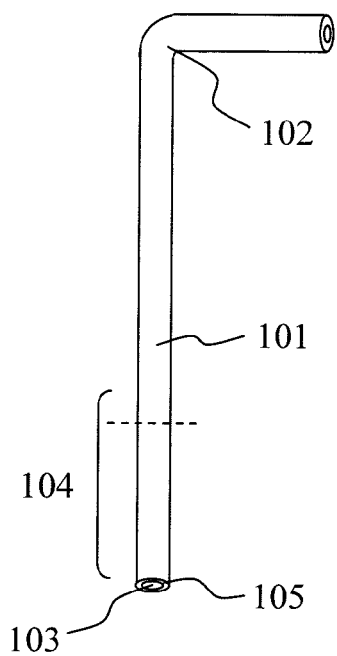
FIG. 1 is a schematic diagram of a dispensing nozzle.

FIG. 1 shows a schematic diagram of a dispensing nozzle. Stainless steel is widely used for a dispensing nozzle main body portion 101 as a material having high corrosion-resistance and good processability. But, the material of the nozzle is not limited to stainless steel and may be a resin, for example, polydimethylsiloxane (PDMS), polyvinyl chloride, or polyacrylate, glass, another metal material (gold, platinum, or copper), or ceramic Here, an example of a dispensing nozzle of stainless steel is shown. The dispensing nozzle is bent at a corner 102 and connected to a suction and discharge mechanism. During the suction of a sample or a reagent, a predetermined amount is sucked into a hollow portion 103. During dispensing, the outer surface of the dispensing nozzle is also immersed in a sample or a reagent. Therefore, regions where a polyethylene glycol (PEG) derivative is chemisorbed and coated are the inner surface, the outer surface, and an end 105 in the case of the dispensing nozzle having the hollow portion 103, and the regions are sufficiently larger than a region 104 that is immersed in a sample or a reagent when the dispensing nozzle dispenses the sample or the reagent.

Examples of a method for chemisorbing the PEG derivative on the surface of the dispensing nozzle include a method using a PEG derivative having a silanol group precursor at one end, as represented by the following general formula (1). A molecule such as general formula (1) is generally referred to as a silane coupling agent, and the molecule can be immobilized on a surface hydroxyl group by a chemical bond. By using such an asymmetrical molecule, the molecule can be orderly immobilized on the surface of the dispensing nozzle as a monomolecular film. In the case of a PEG derivative having silanol group precursors at both ends, the polyethylene glycol chain is immobilized on the surface at both ends, the degree of freedom of motion is lost, and an intrinsic nonspecific adsorption inhibition effect cannot be exhibited in some cases, which is not preferred.

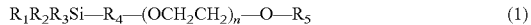

$$R_1R_2R_3Si-R_4-(OCH_2CH_2)_n-O-R_5 \quad (1)$$

$R_1$, $R_2$, and $R_3$ are substituents on silicon (Si). Generally, a substituent on silicon is one selected from the group consisting of ether groups, such as a methoxy group (MeO), an ethoxy group (EtO), and a propyloxy group (PrO), or halogens, such as fluorine (F), chlorine (Cl), bromine (Br), and iodine (I). The substituents on silicon are converted into a silanol group by hydrolysis, and the silanol group is bonded to a hydroxyl group on a solid surface. $R_4$ is a hydrocarbon group. H or $CH_3$ is suitable for $R_5$ in terms of hydrophilicity. n is a positive integer of 2 or more.

A silanol (SiOH) group has high affinity for silicon oxide ($SiO_2$). Glass generally has a SiOH group or a $SiO_2$ layer. Therefore, the silane coupling agent can be immobilized as it is by fabricating a dispensing nozzle with glass. Alternatively, in the case of a dispensing nozzle of a material other than glass, the chemisorption of and a covalent bond to the silane coupling agent can be achieved by previously providing a silicon oxide layer, a glass layer, or the like on the nozzle surface.

As also previously described, stainless steel is widely used for the dispensing nozzles of automatic analyzers in terms of good processability, corrosion-resistance, and the like. Therefore, in an embodiment, an example in which a silicon oxide layer is previously provided on the outermost surface of stainless steel is shown. But, a hydroxyl group is formed on the stainless steel surface, and it is also possible to directly immobilize a silane coupling agent using the place as a reaction point.

Figure 2:
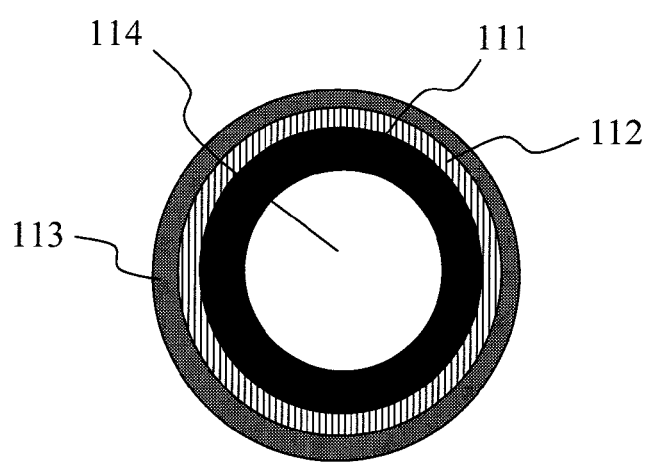
FIG. 2 is a cross-sectional diagram of the dispensing nozzle.

FIG. 2 shows a cross-sectional diagram of the treated portion of the dispensing nozzle treated in this manner, at the position shown by the dotted line in FIG. 1. A dispensing nozzle 111 is a main body portion and is composed of stainless steel or the like. A $SiO_2$ layer 112 is formed on the nozzle 111 by sputtering or CVD film formation or the application and drying of a drug solution (SOG: Spin On Glass, coated glass). A PEG derivative layer 113 is chemically bonded to the $SiO_2$ layer 112 and plays the role of inhibiting the adsorption of biopolymers, such as protein. The dispensing nozzle includes a hollow portion 114. The formed $SiO_2$ layer is washed with alcohol or acid. Then, the $SiO_2$ layer is immersed in a solution of a PEG derivative having a silanol group precursor at one end for a sufficient time. On the thus treated surface, the presence of the carbon-oxygen single (C—O) bond derived from the ethylene glycol chain has been confirmed from a C1s (carbon 1s) XPS measurement result.

For the nozzle of the present invention, an example in which a $SiO_2$ layer is formed only on the nozzle outer wall, and a PEG derivative layer is formed on the outermost surface has been shown. A $SiO_2$ layer and a PEG derivative layer may also be similarly formed on the nozzle inner wall.

The verification of an adsorption inhibition effect is carried out by measuring the amount of adsorption of protein by XPS. Specifically, the amount of adsorption of BSA (bovine serum albumin) is estimated from the peak area in N1s (nitrogen 1s) XPS. BSA is suitable as a model of serum albumin accounting for about 50 to 65% of serum protein. For a substrate subjected to the above surface treatment, it has been confirmed that even after a BSA adsorption experiment, the N1s peak area is equal to or less than the detection limit, and a significant difference from conventional stainless steel and stainless steel on which a $SiO_2$ layer is formed has been seen.

When a liquid level is detected by a dispensing nozzle, an electrical measurement method using a change in its electrostatic capacitance as an indicator is widely used. Therefore, even if an insulating $SiO_2$ thin film layer and an organic film layer on the surface of the insulating $SiO_2$ thin film layer are formed on the surface of a dispensing nozzle made of stainless steel, an electrostatic capacitance change in liquid level detection can be detected. The setting is such that the nozzle stops at about 3 mm below a height position at which the liquid level is detected, and sucks the liquid. In the present invention, the thickness of the $SiO_2$ layer is about 10 nm, and a change in electrostatic capacitance can be easily detected. When some mechanical damage is applied to the nozzle surface, a crack or flaw may occur in the $SiO_2$ layer formed on the nozzle surface. It is possible to include a sensor that notifies a regular maintenance period for the nozzle surface by detecting this crack or flaw in the silicon oxide layer as a change in electrostatic capacitance. In addition, the PEG derivative can be conveniently chemisorbed in the above surface treatment method, and therefore, it is also possible to incorporate into an automatic analyzer a mechanism for chemisorbing a PEG derivative. The use of the dispensing nozzle of the present invention is also useful for integrating an immunity analyzer, which is more sensitive to pollution between samples, with a biochemistry automatic analyzer.

Next, the present invention will be described in detail by Examples, but the present invention is not limited to the following Examples.

EXPERIMENTAL EXAMPLE

First, in order to enhance the reliability of analysis, the effect was verified using a planar substrate. The substrate used was an SUS substrate having a silicon oxide ($SiO_2$) layer having a thickness of 10 nm as the outermost surface layer. The size of the substrate was 10 mm×10 mm×0.5 mm, and for the measurement surface for the verification of the effect, a 10 mm×10 mm surface was used.

(Making of Substrate on which PEG Derivative is Adsorbed)

Figure 3:
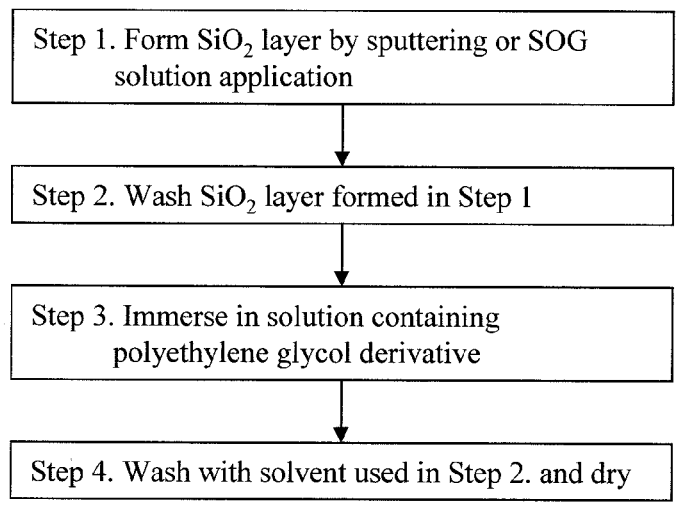
FIG. 3 is a step flow.

FIG. 3 shows the step flow of an experiment.

Step 1. Form $SiO_2$ Layer on SUS Surface.

First, in order to remove grease remaining on a stainless steel (SUS) surface, the SUS surface was degreased with an alkaline solvent. Then, Si was sputtered using a DC magnetron sputtering apparatus using oxygen ($O_2$) as a reactive gas and Ar as a discharge gas. The conditions of $SiO_2$ film formation were as follows. The degree of vacuum reached in the chamber was $5 \times 10^{-5}$ Torr, and the set temperature of the heater was 423 K. As a result, the $SiO_2$ film formation speed was 0.2 nm/second. Thus, a 10 nm $SiO_2$ layer was formed on the SUS surface. The $SiO_2$ layer can be formed by the application and drying of a drug solution (SOG: Spin On Glass, coated glass), rather than sputtering.

Step 2. Wash $SiO_2$ Layer Formed in Step 1.

Specifically, the substrate was ultrasonically washed in ethanol for 15 minutes. In this state, the contact angle against water was measured by Drop Master 500 manufactured by Kyowa Interface Science Co., Ltd. 0.5 µL of pure water was dropped on the substrate surface using a syringe, and the static contact angle after 1 second from the dropping was measured by the three-point method. As a result, the contact angle of the substrate was 10±1°. Thus, it was confirmed that the surface was clean.

Step 3. Immerse in Solution Containing Polyethylene Glycol Derivative.

Specifically, the substrate cleaned in the steps up to step 2 was subjected to silane coupling treatment with 2-[METHOXY(POLYETHYLENEOXY)PROPYL]TRIMETHOXYSILANE. A 3 mM toluene solution of 2-[METHOXY(POLYETHYLENEOXY)PROPYL]TRIMETHOXYSILANE was prepared. Concentrated hydrochloric acid (about 35%) was dropped into the solution at a concentration of 0.8 mL/L, and the solution was stirred. The substrate prepared in step 2 was immersed in the solution of the silane coupling agent thus prepared, for 30 minutes.

2-[METHOXY(POLYETHYLENEOXY)PROPYL]TRIMETHOXYSILANE includes those having a molecular weight of 460 to 590 and includes 6 to 9 ethylene glycol chain units. Here, the chemical formula of 2-[METHOXY(POLYETHYLENEOXY)PROPYL]TRIMETHOXYSILANE is shown below.

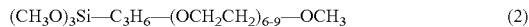

$$(CH_3O)_3Si—C_3H_6—(OCH_2CH_2)_{6-9}—OCH_3 \quad (2)$$

Step 4. Washing and Drying

The substrate was pulled up from the solution, washed once with toluene, washed twice with ethanol, and then water-washed twice and ultrasonically washed in water for 2 minutes. Then, the substrate was dried by nitrogen blowing. Hereinafter, the substrate fabricated in this manner is also referred to as the PEG solution-immersed substrate.

In order to verify the effect of the surface treatment according to the present invention, the following two substrates were prepared for reference.

(Reference Substrate 1. Making of SUS Substrate on Which $SiO_2$ Film Is Formed)

First, the treatment procedure of the first reference substrate will be described. A $SiO_2$ film was formed on a stainless steel substrate by sputtering by the method of step 1 previously described. The film thickness of this $SiO_2$ layer was 10 nm. Next, this plate was ultrasonically washed in ethanol for 15 minutes. In this state, the contact angle against water was measured by a method similar to the above method. As a result, the contact angle of the substrate against water was 10±1°. Thus, it was confirmed that the surface was clean. This substrate on which the $SiO_2$ film was formed was a reference substrate 1.

(Reference Substrate 2. Making of Stainless Steel Substrate)

A stainless steel substrate was prepared as the second reference substrate, ultrasonically washed with a 1% NaOH aqueous solution for 15 minutes, and then ultrasonically washed with ethanol for 15 minutes. This washed stainless steel substrate was a reference substrate 2.

BSA Adsorption Test

A biopolymer adsorption inhibition effect was verified by a BSA (bovine serum albumin) adsorption test. First, a 2.5 g/L solution of BSA was prepared. As the solvent, Dulbecco's Phosphate-Buffered Saline was used. The prepared substrate was immersed in the made solution for 30 minutes. The substrate was pulled up, and then, first sufficiently washed with Dulbecco's Phosphate-Buffered Saline. Then, the substrate was sufficiently washed with pure water. Finally, the substrate was dried by nitrogen blowing.

For the three substrates thus subjected to the BSA adsorption test, XPS measurement was performed, and the surface composition was quantitatively analyzed. The XPS measurement was performed by QuanteraSXM manufactured by PHI. As the X-ray source, monochromatic Al (1486.6 eV) was used. The detection region was Φ100 μm, and the take-off angle was 45°.

As a result of measurement by a wide scan (Binding Energy: 0 to 1275 eV, energy step: 1.0 eV), Fe (iron) and Cr (chromium) were detected from the reference substrate 2. Silicon (Si) and oxygen (O) were detected from the PEG solution-immersed substrate and the reference substrate 1. Thus, it was confirmed that in both of the two substrates on which a thin film of $SiO_2$ was formed, the surface was coated with silicon oxide.

In order to study the bonding state of carbon, a C1s (carbon 1s) narrow scan was measured over a binding energy range of 278 eV to 296 eV at an energy step of 0.1 eV.

Figure 4:
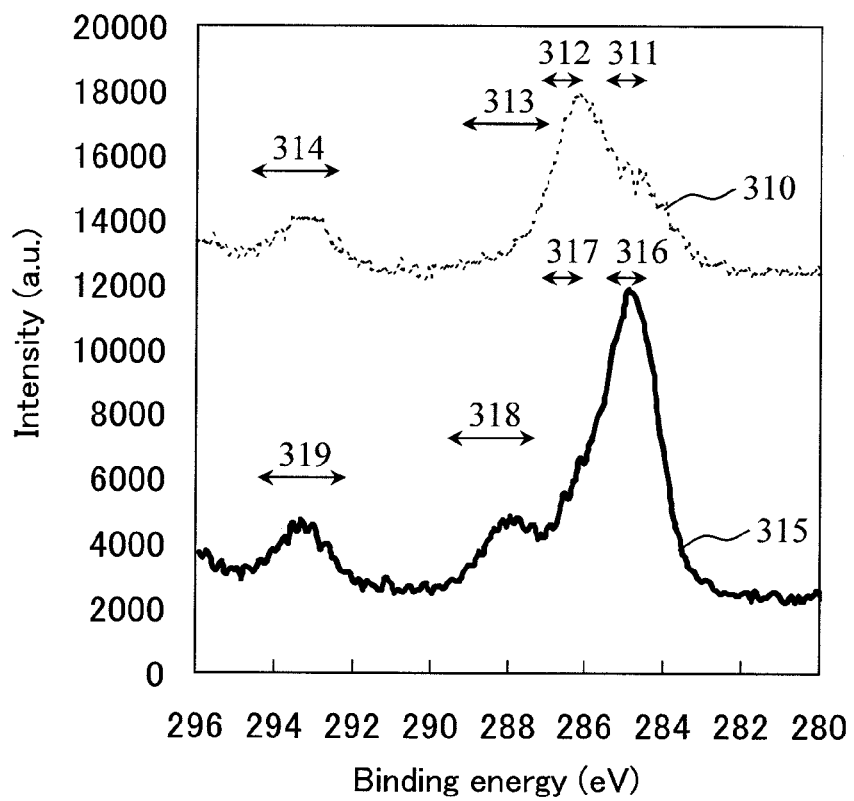
FIG. 4 is a diagram showing XPS results.

The results after the BSA adsorption test were compared. FIG. 4 shows the measurement results of the PEG solution-immersed substrate and the reference substrate 1. The measurement result of the PEG solution-immersed substrate is shown by a broken line 310. The range of an arrow 311 is a range in which C—C and C—H bonds are detected. The range of an arrow 312 is a range in which a C—O bond is detected. The range of an arrow 313 is a range in which C=O, O=C—O, and $CO_3$ bonds are detected. In addition, the range of an arrow 314 is the peak of potassium 2p derived from glass. As shown in FIG. 4, in addition to the peak of C—C and C—H bonds, a peak attributed to a C—O bond was strongly observed. This reflects the C—O bond derived from the ethylene glycol chain in the molecule.

On the other hand, the measurement result of the reference substrate 1 is shown by a solid line 315. The range of an arrow 316 is a range in which C—C and C—H bonds are detected. The range of an arrow 317 is a range in which a C—O bond is detected. The range of an arrow 318 is a range in which C=O, O=C—O, and $CO_3$ bonds are detected. In addition, the range of an arrow 319 is the peak of potassium 2p derived from glass.

As is clear from the Figure, it is seen that in the PEG solution-immersed substrate, the C—O bond detected in the range of the arrow 312 is sufficiently larger than that in the reference substrate 1 on which only the $SiO_2$ film is formed. Therefore, it was confirmed that the PEG derivative was properly immobilized on the PEG solution-immersed substrate.

Next, the comparison of the amount of adsorption of BSA for each substrate will be described. The adsorption of BSA on the stainless steel surface can be quantitatively analyzed from an N is peak corresponding to the nitrogen atom (N) in the BSA by XPS. Here, the N is peak is attributed to amine and amide contained in the BSA. Therefore, in this Example, the relative amount of adsorption of BSA for each substrate was quantified from the amount of N1s, and the effect of inhibiting the adsorption of protein on the substrate surface was verified.

Figure 5:
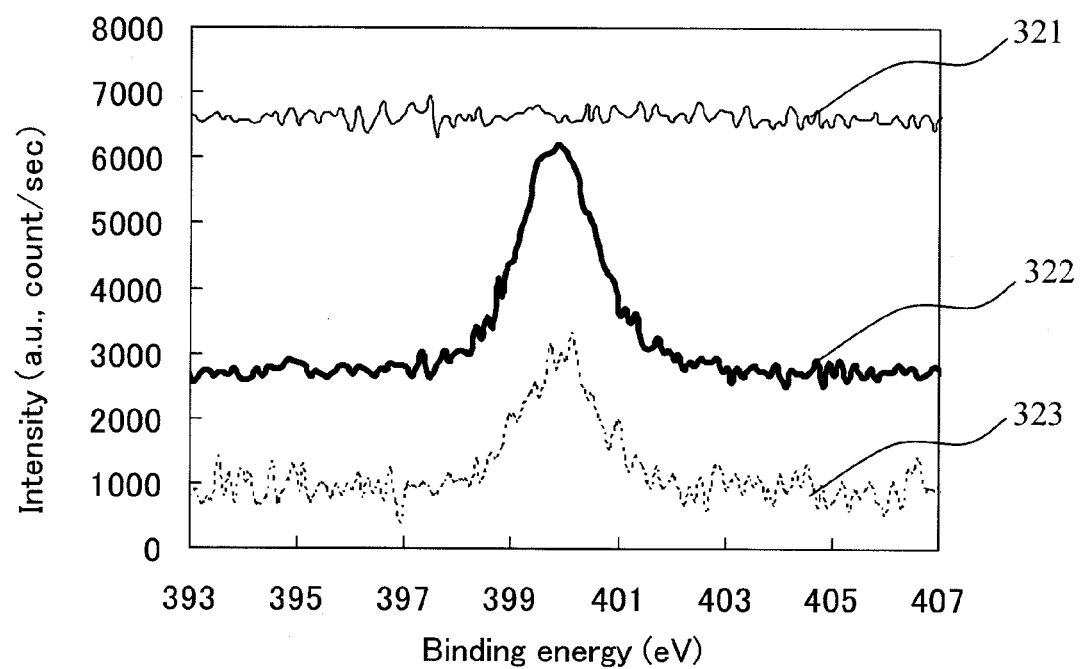
FIG. 5 is a diagram showing XPS results.

The results are shown in FIG. 5. A thin line 321 denotes the spectrum of the PEG solution-immersed substrate, a thick line 322 denotes the spectrum of the reference substrate 1, and a broken line 323 denotes the spectrum of the reference substrate 2. On the surface of the substrate having the $SiO_2$ layer (the reference substrate 1) and the surface of the stainless steel substrate (the reference substrate 2), on which BSA was adsorbed, a symmetrical N is peak having a peak around a binding energy of 400 eV was observed.

The N1s peak area was analyzed by linearly subtracting the background over 395 eV to 405 eV. The N1s surface element concentration (atomic %) obtained from the peak area of each element is shown in Table 1. In Table 1, the substrate immersed in the 2-[METHOXY(POLYETHYLENEOXY)PROPYL]TRIMETHOXYSILANE solution is a PEG solution-immersed substrate, the reference substrate 1 having only $SiO_2$ is a $SiO_2$/SUS substrate, and the reference substrate 2 is a stainless steel substrate.

TABLE 1

| Substrate | N1s surface element concentration (atomic %) |
|---|---|
| (1) PEG solution-immersed substrate | Detection limit (0.1) or less |
| (2) $SiO_2$ film/SUS substrate | 5.0 |
| (3) Stainless steel substrate | 3.0 |

The nitrogen ratio in the SUS substrate on which the $SiO_2$ film was formed was 5.0%, and in the PEG solution-immersed substrate, N1s was equal to or less than the detection limit In addition, in the stainless steel substrate, the nitrogen surface element concentration was 3.0%. Considering the detection limit (0.1% in the content of nitrogen) in this measurement, it was confirmed that in the PEG solution-immersed substrate, the amount of adsorption of BSA was 1/50 or less with respect to the substrate on which the $SiO_2$ film was formed, and the adsorption of BSA was inhibited. In addition, it was confirmed that in the PEG solution-immersed substrate, the amount of adsorption of BSA was 1/30 or less with respect to the stainless steel substrate, and the adsorption of BSA was inhibited.

From the above results, it has been shown that the adsorption of biopolymers, typified by protein, on the dispensing nozzle surface is significantly inhibited by forming a $SiO_2$ layer on stainless steel and chemisorbing a 2-[METHOXY (POLYETHYLENEOXY)PROPYL]TRIMETHOXYSILANE molecule.

As one example of a silane coupling agent having an ethylene glycol chain, the molecule represented by the above chemical formula (2) has been used, but the molecule that can be used in the present invention is not limited to the above chemical formula (2). Chemical formula (2) is a mixture in which the number of ethylene glycol chains (ethylene oxide groups) is 6 to 9. From the requirements that the required number of ethylene oxide groups is 2 or more and that the molecular interaction for molecules to be arranged is sufficient, it is desired that the molecular weight of the PEG derivative is 100 or more. On the contrary, if the steric repulsive force between molecules is too large, the amount of adsorption of the PEG derivative on the surface is reduced. Therefore, it is desired that the molecular weight of the PEG derivative is 20000 or less. The chemical structure of the coating PEG derivative need not be single and may be a mixture.

In addition, the end of this molecule opposite to the silanol group may be a hydroxyl group (OH) or an ether group (O—R, R: an alkyl group). A propyl group ($C_3H_6$) may generally be a hydrocarbon group. Therefore, what is effective for the nozzle surface of the present invention is a molecule represented by the following general formula (3):

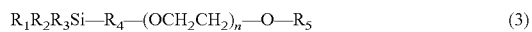

$R_1$, $R_2$, and $R_3$ are substituents on silicon (Si). Generally, a substituent on silicon is one selected from the group consisting of ether groups, such as a methoxy group (MeO), an ethoxy group (EtO), and a propyloxy group (PrO), or halogens, such as fluorine (F), chlorine (Cl), bromine (Br), and iodine (I). The substituents on silicon are converted into a silanol group by hydrolysis, and the silanol group is bonded to a hydroxyl group on a solid surface. $R_4$ is a hydrocarbon group. H or $CH_3$ is suitable for $R_5$ in terms of hydrophilicity. Having a polyethylene glycol chain is useful for protein adsorption inhibition, and other moieties, for example, $R_4$ may be an ether group, a carboxyl group, a carbonyl group, an ester group, an amide group, or the like other than a hydrocarbon group. n is a positive integer of 2 or more.

Example 1

In this Example, a case where a dispensing nozzle is subjected to treatment similar to that in the experimental example will be described. First, a $SiO_2$ layer was formed on the surface of a dispensing nozzle made of stainless steel by sputtering by a method similar to that in the experimental example. The regions to be treated were the end 105, and the region 104 to be immersed in a sample, in the dispensing nozzle in FIG. 1. In this Example, the treated nozzle tip portion had an outer diameter of 0.5 mm and an inner diameter of 0.3 mm, and the $SiO_2$ layer was formed with a thickness of 10 nm on a 10 mm tip region. It is also possible to treat the entire surface of the dispensing nozzle, but by limiting the regions to be treated to the portions to be immersed, the cost can be reduced.

Next, the surface of the dispensing nozzle on which the $SiO_2$ layer was formed was ultrasonically washed with ethanol for 15 minutes. At this time, a support was provided for disposition in which the nozzle is not in contact with the container, so that the nozzle is not damaged by ultrasonic.

The dispensing nozzle after the cleaning treatment was immersed in a solution of a PEG derivative. Specifically, a 3 mM toluene solution of 2-[METHOXY(POLYETHYLENEOXY)PROPYL]TRIMETHOXYSILANE was prepared, and concentrated hydrochloric acid (about 35%) was dropped into the solution at a concentration of 0.8 mL/L. The washed dispensing nozzle was immersed in the silane coupling agent solution thus prepared, for 30 minutes. The dispensing nozzle was pulled up from the solution, washed once with toluene, washed twice with ethanol, and then water-washed twice and ultrasonically washed in water for 2 minutes. Then, the dispensing nozzle was dried by nitrogen blowing.

For the verification of the effect, the amount of BSA remaining on the surface was measured by XPS as in the experimental example. As a result, it was confirmed that the protein remaining on the dispensing nozzle surface after dispensing was reduced to 1/50 or less (the XPS measurement detection limit described in the experimental example, or less) compared with a conventional nozzle made of stainless steel.

Example 2

Figure 6:
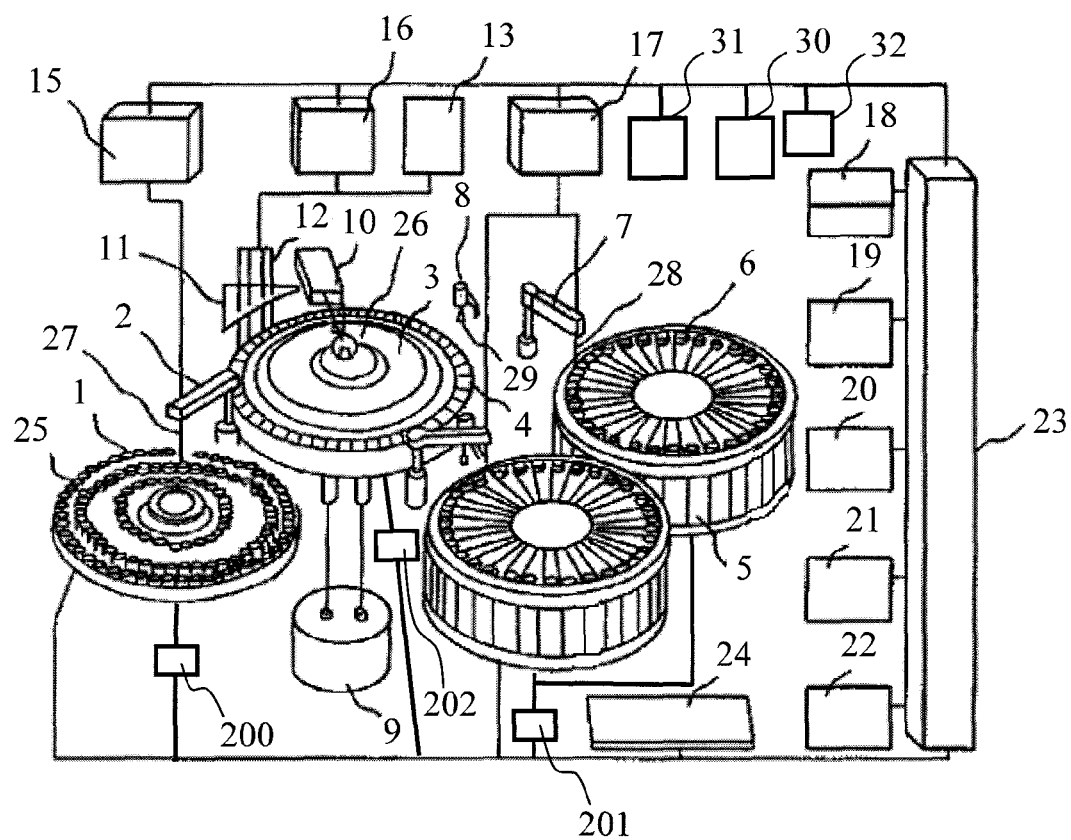
FIG. 6 is a diagram showing an example of the configuration of an automatic analyzer.

FIG. 6 is a diagram showing an example of the configuration of an automatic analyzer according to the present invention. Next, its basic configuration will be described. One or more sample containers 25 are disposed in a sample-containing portion mechanism 1. Here, an example of a sample disk mechanism, which is a sample-containing portion mechanism included in a disk-shaped mechanism portion, will be described. But, another form of the sample-containing portion mechanism may be the form of a sample rack or a sample holder generally used in an automatic analyzer. In addition, a sample here refers to a solution to be examined, which is used for reaction in a reaction container, and may be an undiluted solution of a collected sample and may be a solution obtained by subjecting the undiluted solution to processing treatment, such as dilution or pretreatment. A sample in the sample container 25 is extracted and injected into a predetermined reaction container by the sample dispensing nozzle 27 of a dispensing mechanism for sample supply 2. The sample dispensing nozzle is surface-treated with 2-[METHOXY (POLYETHYLENEOXY)PROPYL]TRIMETHOXYSILANE by the method described in Example 1. A reagent disk mechanism 5 includes a large number of reagent containers 6. In addition, a dispensing mechanism for reagent supply 7 is disposed in the mechanism 5, and a reagent is sucked and injected into a predetermined reaction Cell by the reagent dispensing nozzle 28 of this mechanism 7. Reference numeral 10 denotes a spectrophotometer, and reference numeral 26 denotes a light source with a light-collecting filter. A reaction disk 3 for containing objects to be measured is disposed between the spectrophotometer 10 and the light source with a light-collecting filter 26. For example, 120 reaction Cells 4 are mounted on the outer periphery of this reaction disk 3. In addition, the entire reaction disk 3 is maintained at a predetermined temperature by a thermostat 9. Reference numeral 11 denotes a reaction Cell washing mechanism. A washing agent is supplied from a washing agent container 13, and suction in the Cell is performed by a suction nozzle 12.

Reference numeral 19 denotes a computer, reference numeral 23 denotes an interface, reference numeral 18 denotes a Log converter and A/D converter, reference numeral 17 denotes a reagent pipetter, reference numeral 16 denotes a wash water pump, and reference numeral 15 denotes a sample pipetter. In addition, reference numeral 20 denotes a printer, reference numeral 21 denotes a CRT, reference numeral 22 denotes a flexible disk or a hard disk as a storage device, and reference numeral 24 denotes an operation panel. The sample disk mechanism, the reagent disk mechanism, and the reaction disk are controlled and driven by a drive portion 200, a drive portion 201, and a drive portion 202, respectively, via the interface. In addition, each portion of the automatic analyzer is controlled by the computer 19 via the interface.

In the above-described configuration, an operator inputs analysis request information using the operation panel 24. The analysis request information input by the operator is stored in a memory in the microcomputer 19. A sample to be measured, which is placed in the sample container 25 and set at a predetermined position in the sample-containing portion mechanism 1, is dispensed in a predetermined amount into a reaction Cell by the sample pipetter 15 and the surface-treated sample dispensing nozzle 27 of the dispensing mechanism for sample supply 2 according to the analysis request information stored in the memory of the microcomputer 19. The surface-treated sample dispensing nozzle 27 is water-washed, and used for dispensing the next sample.

At this time, by using the sample dispensing nozzle 27 coated with 2-[METHOXY(POLYETHYLENEOXY)PROPYL]TRIMETHOXYSILANE, it is possible to inhibit the adsorption of biopolymers typified by protein and reduce carry over between samples to 1/2 or less compared with a conventional dispensing nozzle made of stainless steel. The carry over is compared after washing. Therefore, it is a significant advance that although it is difficult to further decrease the carry over, the carry over rate can be decreased by surface-treating the nozzle. In addition, at this time, 2-[METHOXY (POLYETHYLENEOXY)PROPYL]TRIMETHOXYSILANE forms a monomolecular film, and the $SiO_2$ layer on the nozzle surface is 10 nm and thin, and therefore, liquid level detection can be performed using a change in electrostatic capacitance. A predetermined amount of a reagent is dispensed into the reaction Cell by the reagent dispensing nozzle 28 of the dispensing mechanism for reagent supply 7. The reagent dispensing nozzle 28 is water-washed, and then dispenses the reagent for the next reaction Cell. A mixed liquid of the sample and the reagent is stirred by the stirring bar 29 of a stirring mechanism 8. The stirring mechanism 8 sequentially stirs a mixed liquid in the next reaction Cell.

In addition, a solution of at least one molecule selected from the group of a series of molecules represented by general formula (1) in the experimental example can be used for the surface treatment of the sample dispensing nozzle 27.

Here, the principle of liquid level detection included in this apparatus will be described. An electrostatic capacitance mode is used for the principle of the included liquid level detection. In the electrostatic capacitance mode, the electrostatic capacitance value between the nozzle and a ground (corresponding to a Cell bottom in the case of this Example) is measured. The electrostatic capacitance mode uses the fact that when the nozzle is in contact with a substance having a high dielectric constant, the electrostatic capacitance is larger than that in air.

Figure 7:
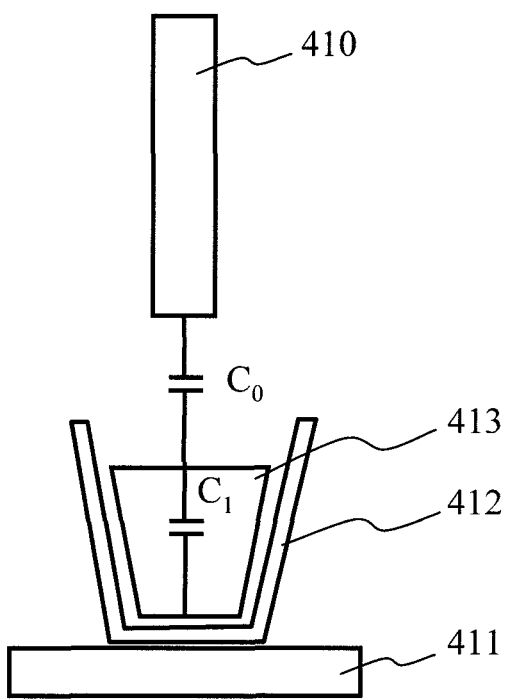
FIG. 7 is a conceptual diagram of liquid level detection.

FIG. 7 shows a conceptual diagram of liquid level detection according to the electrostatic capacitance mode, which is a case where a metal nozzle that is not surface-modified is used. A metal nozzle 410 is not in contact with a sample 413 in a sample container 412. When an apparatus main body 411 in contact with the sample container is a ground, the electrostatic capacitance between the nozzle and the ground is determined by the electrostatic capacitance $C_o$ of air and the electrostatic capacitance $C_1$ of water. The total electrostatic capacitance C at this time is $C=(C_0 \times C_1)/(C_0+C_1)$.

Figure 8:
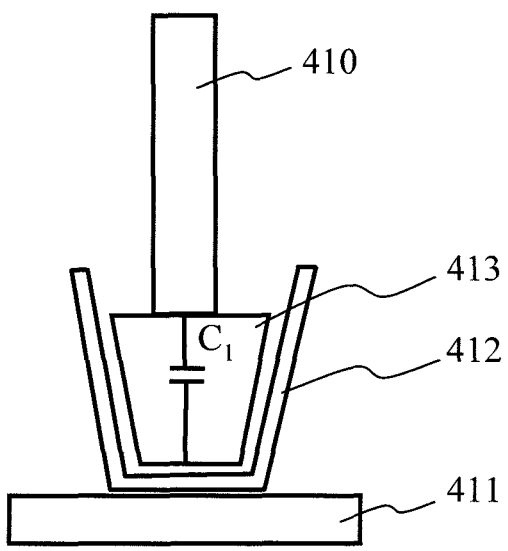
FIG. 8 is a conceptual diagram of liquid level detection.

On the other hand, FIG. 8 shows a conceptual diagram of a case where the nozzle is in contact with the liquid level. The metal nozzle 410 is in contact with the liquid 413 in the sample container 412. When the apparatus main body 411 is a ground for the sample container, the electrostatic capacitance between the nozzle and the ground is $C_1$.

Figure 9:
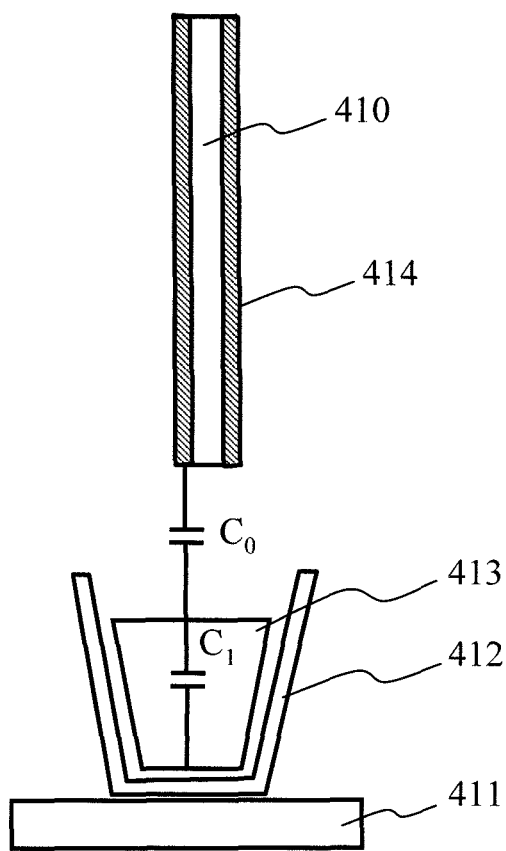
FIG. 9 is a conceptual diagram of liquid level detection.

By using this mode, liquid level detection can be performed even by the $SiO_2$-coated nozzle in this Example. FIG. 9 shows an example of liquid level detection by a silicon oxide-coated nozzle. A case where a metal nozzle 410 having a silicon oxide layer 414 is not in contact with a liquid 413 in a sample container 412 is shown. An apparatus main body 411 in contact with the sample container is a ground. The electrostatic capacitance of the silicon oxide ($SiO_2$) layer is $C_2$. When the electrostatic capacitance when the $SiO_2$-coated nozzle is in air is $C_x$, $1/C_x=1/C_0+1/C_1+1/C_2$ holds.

Figure 10:
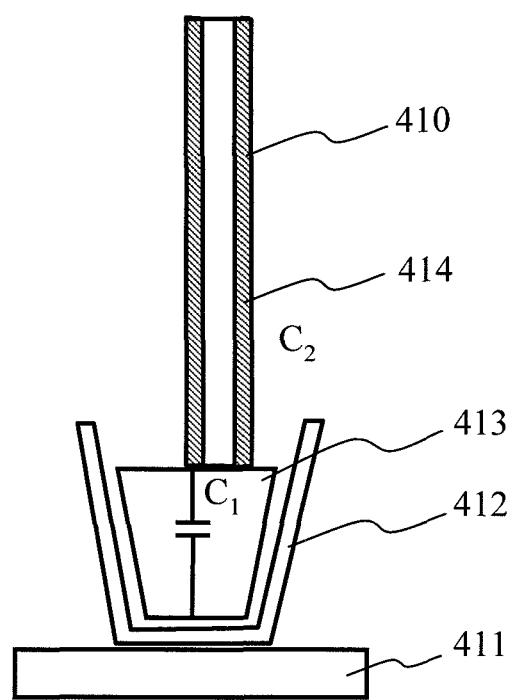
FIG. 10 is a conceptual diagram of liquid level detection.

On the other hand, FIG. 10 shows a case where the metal nozzle 410 having the silicon oxide layer 414 is in contact with the liquid 413 in the sample container 412. The apparatus main body 411 in contact with the sample bottle is a ground. The electrostatic capacitance of the silicon oxide ($SiO_2$) layer is $C_2$. When the electrostatic capacitance when the $SiO_2$-coated nozzle is in contact with the liquid level is $C_y$, $1/C_y=1/C_1+1/C_2$ holds, which is different from the electrostatic capacitance $C_x$ in air, and therefore, the liquid level can be detected.

When the $SiO_2$ layer of this nozzle cracks due to some impact or contact, the metal nozzle is in direct contact with air, and therefore, the electrostatic capacitance $C_2$ of the $SiO_2$ layer can be neglected. Then, the electrostatic capacitance changes significantly, and therefore, a flaw or a crack in the $SiO_2$ layer on the nozzle can be detected. When a flaw or a crack in the $SiO_2$ layer occurs, carry over may increase due to the place. Therefore, it is important that a flaw or a crack in the $SiO_2$ layer can be detected. In addition, there is a storage medium 32 that also stores a case where the deviation of electrostatic capacitance from the initial value exceeds a certain threshold, and the change of the initial value accompanying nozzle replacement.

The automatic analyzer in this Example includes a detection mechanism 31 for detecting this change in electrostatic capacitance, and an indicator 30 for notifying a nozzle replacement period and analysis accuracy. This indicator shows a blue color during a normal period, and a change in electrostatic capacitance is always measured. When an abnormality, such as a crack or a flaw, occurs in the silicon oxide layer on the nozzle surface, the abnormality is detected from a change in electrostatic capacitance, and the indicator 30 is indicated, for example, in red, for information via the interface. In addition, the data of the sample analyzed at this time is stored in the apparatus, and a program for reacquiring analysis data after nozzle replacement is included.

Example 3

Figure 11:
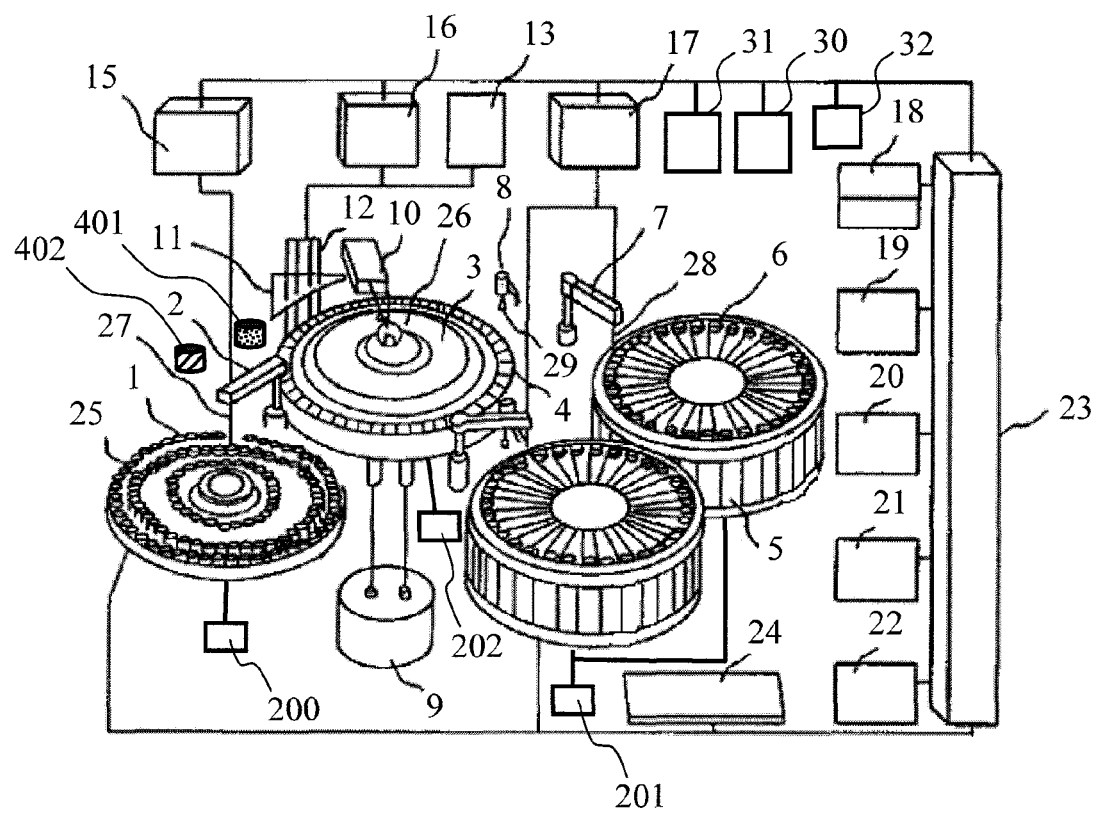
FIG. 11 is a diagram showing an example of the configuration of an automatic analyzer including a mechanism for performing surface treatment.

FIG. 11 shows a schematic diagram of an automatic analyzer used in this Example. In this Example, a first treatment liquid vessel 401 and a second treatment liquid vessel 402 are added to the configuration of the automatic analyzer shown in FIG. 6. In addition, a dispensing nozzle 27 in FIG. 11 is a dispensing nozzle made of stainless steel, and one on the surface of which a 10 nm $SiO_2$ layer is formed is used.

First, the sample dispensing nozzle 27 is rotationally moved to the first treatment liquid vessel 401, lowered, and immersed in a first treatment liquid. The immersed region at this time is sufficiently larger than a region where the sample dispensing nozzle 27 is immersed in a sample during dispensing. As the first treatment liquid, a solution of 2-[METHOXY(POLYETHYLENEOXY)PROPYL]TRIMETHOXYSILANE or at least one molecule selected from the group of the series of molecules represented by general formula (1) in the experimental example, as a PEG derivative, can be used. Here, a 2 mM toluene solution of 2-[METHOXY(POLYETHYLENEOXY)PROPYL]TRIMETHOXYSILANE is used. The immersion time changes according to immersion frequency. For example, when the dispensing nozzle 27 is immersed every time in dispensing, about 1 second is sufficient. In addition, when the dispensing nozzle 27 is immersed after the completion of one-day analysis, it is immersed for about 30 minutes. Next, the dispensing nozzle 27 is rotationally moved to the second treatment liquid vessel 402, lowered, and immersed in a second treatment liquid. At this time, the immersed region is sufficiently larger than the previous region immersed in the first treatment liquid. As the solution used in the second treatment liquid vessel 402, toluene, which is used as the solvent in the previous treatment liquid in the first treatment liquid vessel 401, is used.

Excess 2—[METHOXY(POLYETHYLENEOXY)PROPYL]TRIMETHOXYSILANE that adheres to the dispensing nozzle 27 when the dispensing nozzle 27 is treated in the first treatment liquid vessel 401 can be removed by the above operation in the second treatment liquid vessel 402. By subsequently dispensing a sample, it is possible to inhibit the adsorption of biopolymers typified by protein and reduce carry over to 1/2 or less compared with a conventional dispensing nozzle made of stainless steel. The carry over is compared after washing. Therefore, it is a significant advance that although it is difficult to further decrease the carry over, the carry over rate can be decreased by surface-treating the nozzle.

Also in the above Examples 1 to 3, as in the experimental example, from the requirements that the required number of ethylene oxide groups is 2 or more and that the molecular interaction for molecules to be arranged is sufficient, it is desired that the PEG derivative has a molecular weight of 100 or more. On the contrary, if the steric repulsive force between molecules is too large, the amount of adsorption of the PEG derivative on the surface is reduced. Therefore, it is desired that the molecular weight of the PEG derivative is 20000 or less. The chemical structure of the coating PEG derivative need not be single and may be a mixture.

In the above Examples, carry over in the sample dispensing nozzle has been a problem. But, by performing the treatment of the present invention on all members that can be factors of carry over, such as the stirring bar, a similar effect is obtained.

According to the present invention, dramatically reducing nonspecific adsorption of biopolymers, such as protein, on the dispensing nozzle surface to promote the inhibition of carry over can contribute to an improvement in the reliability of the automatic analyzer. In addition, therefore, it is possible to also contribute to trace amounts of samples and trace amounts of reagents and reduce the running cost and the environmental load.

| | Reference Signs List |
|---|---|
| 1 | sample-containing portion mechanism |
| 2 | dispensing mechanism for sample supply |
| 3 | reaction disk |
| 4 | reaction Cell |
| 5 | reagent disk mechanism |
| 6 | reagent container |
| 7 | dispensing mechanism for reagent supply |
| 8 | stirring mechanism |
| 9 | thermostat |
| 10 | spectrophotometer |
| 11 | reaction Cell washing mechanism |
| 12 | suction nozzle |
| 13 | washing agent container |
| 15 | sample pipetter |
| 16 | wash water pump |
| 17 | reagent pipetter |
| 25 | sample container |
| 26 | light source with a light-collecting filter |
| 27 | sample dispensing nozzle |
| 28 | reagent dispensing nozzle |
| 29 | stirring bar |
| 30 | indicator |
| 31 | detection mechanism |
| 32 | storage medium |
| 101 | dispensing nozzle main body portion |
| 111 | dispensing nozzle main body portion |
| 112 | gold thin film layer |
| 113 | hydrophilic molecular layer |
| 200 | drive portion |
| 201 | drive portion |
| 202 | drive portion |
| 401 | first treatment liquid vessel |
| 402 | second treatment liquid vessel |
| 403 | dispensing nozzle washing vessel |
| 410 | dispensing nozzle |
| 411 | apparatus main body |
| 412 | sample container |
| 413 | sample |
| 414 | silicon oxide layer |

The invention claimed is:
1. An automatic analyzer comprising:
    a plurality of sample containers each containing a sample;
    a plurality of reagent containers each containing a reagent;
    a plurality of reaction Cells into which the samples and the reagents are to be injected;
    a sample dispensing mechanism comprising a sample dispensing nozzle and dispensing the samples in the sample containers into the reaction Cells;
    a reagent dispensing mechanism comprising a reagent dispensing nozzle and dispensing the reagents in the reagent containers into the reaction Cells, and electrostatic capacitance measuring means for measuring electrostatic capacitance between the sample dispensing nozzle and the reaction Cell, wherein the sample dispensing nozzle has a nozzle main body made of metal, and a silicon oxide layer on an outer surface of the nozzle main body, and a silicon derivative having polyethylene glycol, represented by the following general formula:

$Si—R_1—(OCH_2CH_2)_n—O—R_2$ (n is a positive integer of 2 or more, $R_1$ is a hydrocarbon group, and $R_2$ is H or $CH_3$)

is chemisorbed on the silicon oxide layer, and the electrostatic capacitance measuring means measures the electrostatic capacitance via the silicon oxide layer and the silicon derivative.

2. The automatic analyzer according to claim 1, comprising a mechanism for detecting an abnormality of the silicon oxide layer on the sample dispensing nozzle surface based on a change in the electrostatic capacitance; and an indicator for indicating the abnormality on detection of the abnormality.

3. The automatic analyzer according to claim 1, wherein a region of the sample dispensing nozzle where the polyethylene glycol derivative is chemisorbed is larger than a region where the sample dispensing nozzle is immersed in the sample during dispensing operation.

4. The automatic analyzer according to claim 1, comprising a mechanism for chemisorbing the polyethylene glycol derivative on the sample dispensing nozzle.

5. The automatic analyzer according to claim 1, wherein the polyethylene glycol derivative is a 2-methoxypolyethyleneoxysilane derivative.

6. A method for manufacturing a dispensing nozzle for the automatic analyzer of claim 1 used for dispensing a sample in a sample container into a reaction cell and measuring distance from the sample in the reaction cell by electrostatic capacitance detection, comprising the steps of:

forming a silicon oxide layer on a surface of a metal nozzle using sputtering or drug solution application and drying;

washing the silicon oxide layer formed on the surface of the metal nozzle;

immersing the washed dispensing nozzle in a solution of a polyethylene glycol derivative having a silanol group precursor, represented by the following general formula: $R_1R_2R_3Si—R_4—(OCH_2CH_2)_n—O—R_5$ ($R_1$, $R_2$, and $R_3$ are substituents on silicon, $R_4$ is a hydrocarbon group, $R_5$ is H or $CH_3$, and n is a positive integer of 2 or more);

washing the treated surface of the metal nozzle with a solvent; and drying the washed surface of the dispensing nozzle.

* * * * *